(12) United States Patent
Atherton

(10) Patent No.: US 6,776,889 B2
(45) Date of Patent: Aug. 17, 2004

(54) CORROSION MONITORING

(76) Inventor: Eric Atherton, 83 Wroslyn Road, Freeland, Witney, Oxfordshire, OX8 8HL (GB)

( * ) Notice: Subject to any disclaimer, the term of this patent is extended or adjusted under 35 U.S.C. 154(b) by 0 days.

(21) Appl. No.: 10/069,347

(22) PCT Filed: Jun. 8, 2001

(86) PCT No.: PCT/GB01/02543
§ 371 (c)(1),
(2), (4) Date: Jun. 7, 2002

(87) PCT Pub. No.: WO01/98753
PCT Pub. Date: Dec. 27, 2001

(65) Prior Publication Data
US 2002/0153249 A1 Oct. 24, 2002

(30) Foreign Application Priority Data
Jun. 23, 2000 (GB) .............................................. 0015349

(51) Int. Cl.⁷ ........................ G01N 27/403; G01N 17/02
(52) U.S. Cl. ..................... 204/404; 204/406; 205/775.5
(58) Field of Search ................................ 204/904, 406, 204/412; 205/775.5, 777; 324/700, 71.2

(56) References Cited

U.S. PATENT DOCUMENTS

| | | |
|---|---|---|
| 3,661,751 A | 5/1972 | Wilson |
| 3,716,460 A | 2/1973 | Weistuch et al. |
| 3,788,962 A | 1/1974 | Frenck |
| 3,855,101 A * | 12/1974 | Wilson ........................ 204/406 |
| 4,130,464 A * | 12/1978 | Kanno et al. ................ 205/777 |
| 5,139,627 A | 8/1992 | Eden et al. |
| 6,280,603 B1 * | 8/2001 | Jovancicevic ............ 205/775.5 |

FOREIGN PATENT DOCUMENTS

WO    WO 00 34760 A    6/2000

* cited by examiner

Primary Examiner—Kaj K. Olsen
(74) Attorney, Agent, or Firm—Lahive & Cockfield, LLP

(57) ABSTRACT

A corrosion monitor comprising electronic circuitry arranged such that DC current flowing between two electrodes is reduced to essentially zero, while allowing any naturally occurring AC current noise to flow unhindered and be monitored by the instrumentation. The two electrodes consist of one inert reference electrode, and one electrode constructed of the material to be monitored (the working electrode). Even though the two electrodes will have different galvanic potentials, by reducing the DC current to zero the electronic circuitry is able to avoid galvanic effects. Furthermore, the voltage potential can be monitored between the inert current reference electrode, and a third electrode also constructed of an inert material. As corrosion activity occurs on the working electrode, both current noise and voltage noise may then be monitored simultaneously.

6 Claims, 2 Drawing Sheets

US 6,776,889 B2

CORROSION MONITORING

RELATED APPLICATIONS

This application is a 35 U.S.C. 371 national stage filing of, and claims priority to, International Application No. PCT/GB01/02543, filed Jun. 8, 2001, which in turn claims priority to Great Britain Patent Application No. 0015349.4 filed on Jun. 23, 2000 in Great Britain. The contents of the aforementioned applications are hereby incorporated by reference.

FIELD OF THE INVENTION

The present application relates to corrosion monitoring.

BACKGROUND ART

Corrosion causes enormous economic loss to industry. The ability to monitor the rate of corrosion allows corrective and preventative action to be taken and can minimise or alleviate this cost. One method of monitoring corrosion is to measure and analyse the naturally occurring currents and voltages that are generated in corroding materials.

Iverson ("Transient Voltage changes produced in corroding metals and alloys", Electrochemical Science, June 1968) used a high impedance voltmeter and a filter to block DC voltage, to monitor this electrochemical voltage noise, and related this to the action of chemical inhibitor on a corroding electrode.

Eden, Hladky and John ("Corrosion 86 Paper 274", March 1986) used a ZRA (zero resistance ammeter) to monitor electrochemical current noise flowing between two identical, corroding electrodes. This paper also discloses how, with the addition of a third voltage reference electrode (either of the same material, or of an inert, non-corroding material), current noise and voltage noise can be measured simultaneously. This paper also discloses various statistical methods to process the current and voltage noise, including moving the data from the time domain to the frequency domain using an FFT (fast Fourier transform).

Known electrochemical noise systems use a ZRA to measure current noise. This requires the two electrodes connected to the ZRA to be of similar material, so that they have the same galvanic potential. Connecting dissimilar materials to a ZRA will tend to produce artificially large circulating currents and corrosion, due to the difference in galvanic potential. Thus both electrodes are constructed of the same material as the pipe or vessel that is to be monitored. One disadvantage of this is that it is not possible to determine the direction of the current flow that is causing corrosion, as an anodic reaction on one electrode will produce the same reaction as a cathodic reaction on the other electrode. Furthermore, in practice, probes have a tendency to "bridge" with corrosion products and scale, and having to have at least two electrodes that are subject to corrosion encourages this failure mechanism.

SUMMARY OF THE INVENTION

The present invention seeks to enable electrochemical current noise to be continuously monitored using two dissimilar electrode materials, so that only one electrode need be constructed of the corrodable material. The present invention further seeks to enable electrochemical current and potential noise to be continuously monitored using at least 3 electrodes, only one of which is necessarily constructed of corrodable material.

According to the present invention, a corrosion monitor comprises electronic circuitry arranged such that DC current flowing between two electrodes is reduced to essentially zero, while allowing any naturally occurring AC current noise to flow unhindered and be monitored by the instrumentation.

The two electrodes consist of one inert reference electrode, and one electrode constructed of the material to be monitored (the working electrode). Even though the two electrodes will have different galvanic potentials, by reducing the DC current to zero the electronic circuitry is able to avoid galvanic effects.

Furthermore, the voltage potential can be monitored between the inert current reference electrode, and a third electrode also constructed of an inert material. As corrosion activity occurs on the working electrode, both current noise and voltage noise may then be monitored simultaneously.

It is important to note that only one electrode need be made of the material to be monitored, in which case all current and voltage noise is associated with the activity on this one electrode.

In practice, the corrosion monitor can comprise an inert reference electrode and a working electrode of the material to be monitored, and a voltage follower adapted to apply a voltage between the electrodes, which voltage reflects previous values of the current flowing between the electrodes. This voltage is preferably proportional to an integration of this current.

The current flowing between the electrodes can be measured and that output can then be fed to an integrating circuit. This will produce an output which can be fed to the voltage follower for application to the working electrode. Measurement of the current can be by simply detecting the voltage drop across a resistance or other impedance.

BRIEF DESCRIPTION OF THE DRAWINGS

The present invention will now be illustrated by way of example, with reference to the accompanying figures, in which.

DETAILED DESCRIPTION OF THE EXAMPLE

Figure 1:
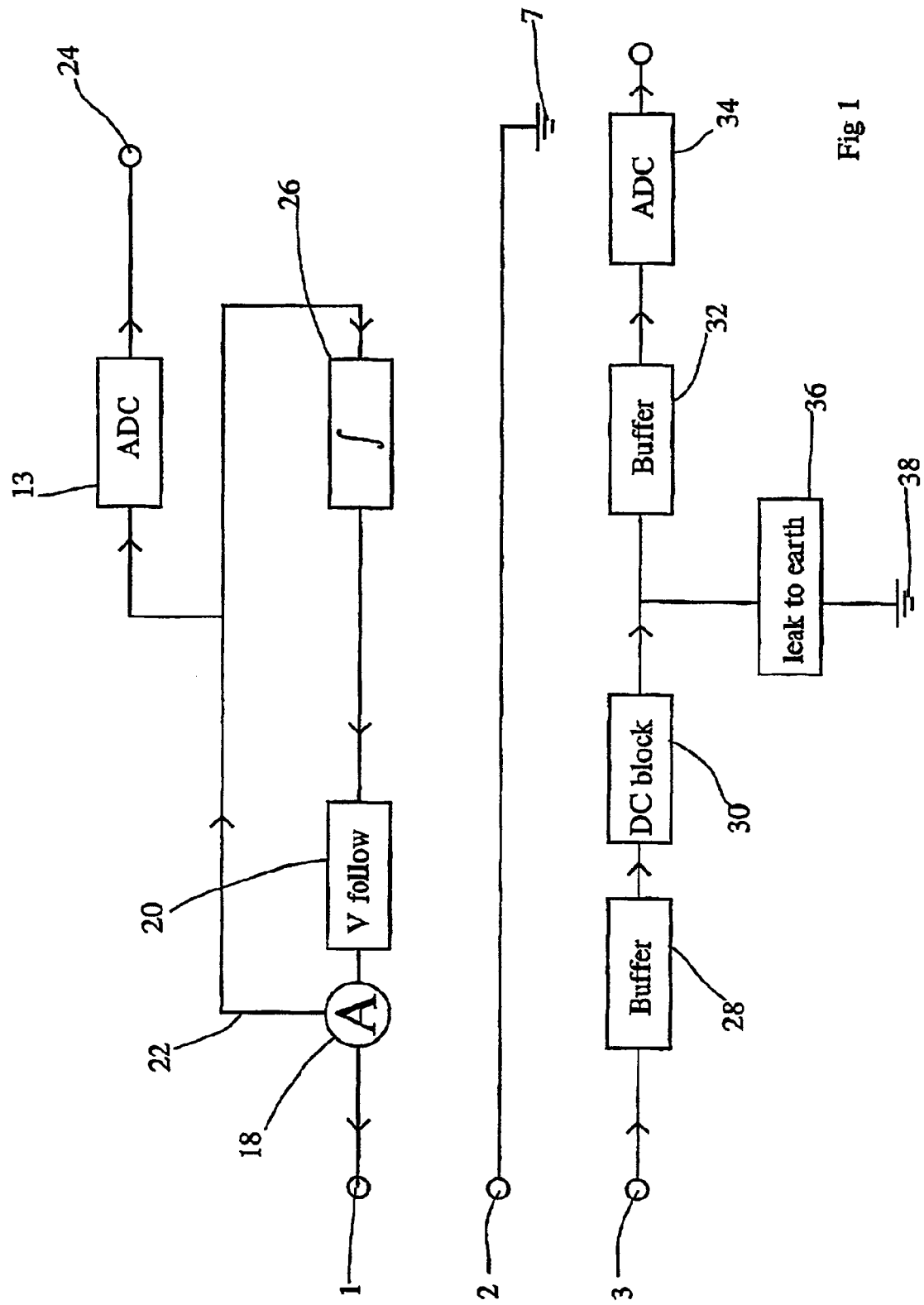
FIG. 1 is a schematic block diagram of an corrosion monitor according to the present invention.

FIG. 1 shows three electrodes, 1, 2 and 3 that are immersed in a potentially corrosive solution. Electrode 1 is the working electrode and is constructed of the material of the pipe or vessel that is being monitored. This can be adjacent the item, or can be an isolated part of the item, or can be the item itself if dimensions permit. Thus, any corrosion activity in the pipe of vessel will be duplicated on electrode 1. Reference electrodes 2 and 3 are constructed of an inert material that does not corrode such as Inconel™, Hastelloy™, or a precious metal, for example. This minimises any current and voltage noise that may be introduced into the system from this source.

A voltage follower 20 has its output connected to the working electrode 1 such that the electrode is thus set to the output of the follower 20. The output of the voltage follower is set in a manner which will be described below.

An ammeter 18 is also provided between the follower 20 and the electrode 1 to measure the current flowing to or from the electrode 1 and produce a signal 22 which reflects this. This signal is fed to a Analogue to Digital Converter (ADC) 13 to form the measured current output 24 of the monitor. The signal is also fed to an integrator 26 which compares it to a ground reference 7 or other stable voltage. The output of the integrator is fed to the voltage follower 20 and the same voltage is thus applied to the working electrode 1.

As a result, if there is a galvanic potential between the electrodes when the system is started, then a potential difference will exist which will generate a galvanic current. This will be detected by the ammeter 18 and fed to the integrator 26. For so long as there is a current flowing in this way, the output of the integrator 26 will rise (or fall, depending on the sign of the current) thereby reducing the current flow provided the signs of the components are set correctly. Eventually, the natural galvanic potential difference between the electrodes will be matched by the voltage output of the integrator, and no current will flow in the quiescent state.

From then on, when there is a corrosion event on the working electrode 1, this will give rise to a transient current which will be detected by the ammeter 18 and fed to the ADC 13. However, there will be no long term current arising from the galvanic difference between the working electrode 1 and the reference electrode 2 (hereinafter the "current reference electrode"). This allows different materials to be used in their construction, avoiding the difficulties noted above.

In an alternative arrangement, the output of the ADC 13 could be integrated or otherwise processed via a digital processor and fed back via a DAC (digital to analogue converter) to the input of the voltage follower 20. The ammeter 18 and/or the follower 20 could also be provided elsewhere in the circuit, such as between the reference electrode and the integrator.

An advantage of integrating the signal digitally is that other signals such as a low frequency variation can be added, such as at 0.1 Hz. The effect of this added signal could be distinguished from the electrochemical noise by (for example) suitable filters or FFT analysis. This could yield information as to corrosion rates by comparing the polarisation current and polarisation voltages using well-known techniques.

FIG. 1 also shows the voltage measurement function of the monitor. The further reference electrode 3 (hereinafter the "voltage reference electrode") is linked to a buffer 28 to avoid current drain on the voltage reference electrode. The output of this is linked to a DC block 30 which allows AC and transient signals to pass but blocks steady DC voltages. The signal thus filtered is fed to a further buffer 32, the output of which is converted to an output digital signal by ADC 34. The average output of the DC block is held at zero potential via a high impedance leak path 36 to an earth reference 38.

Figure 2:
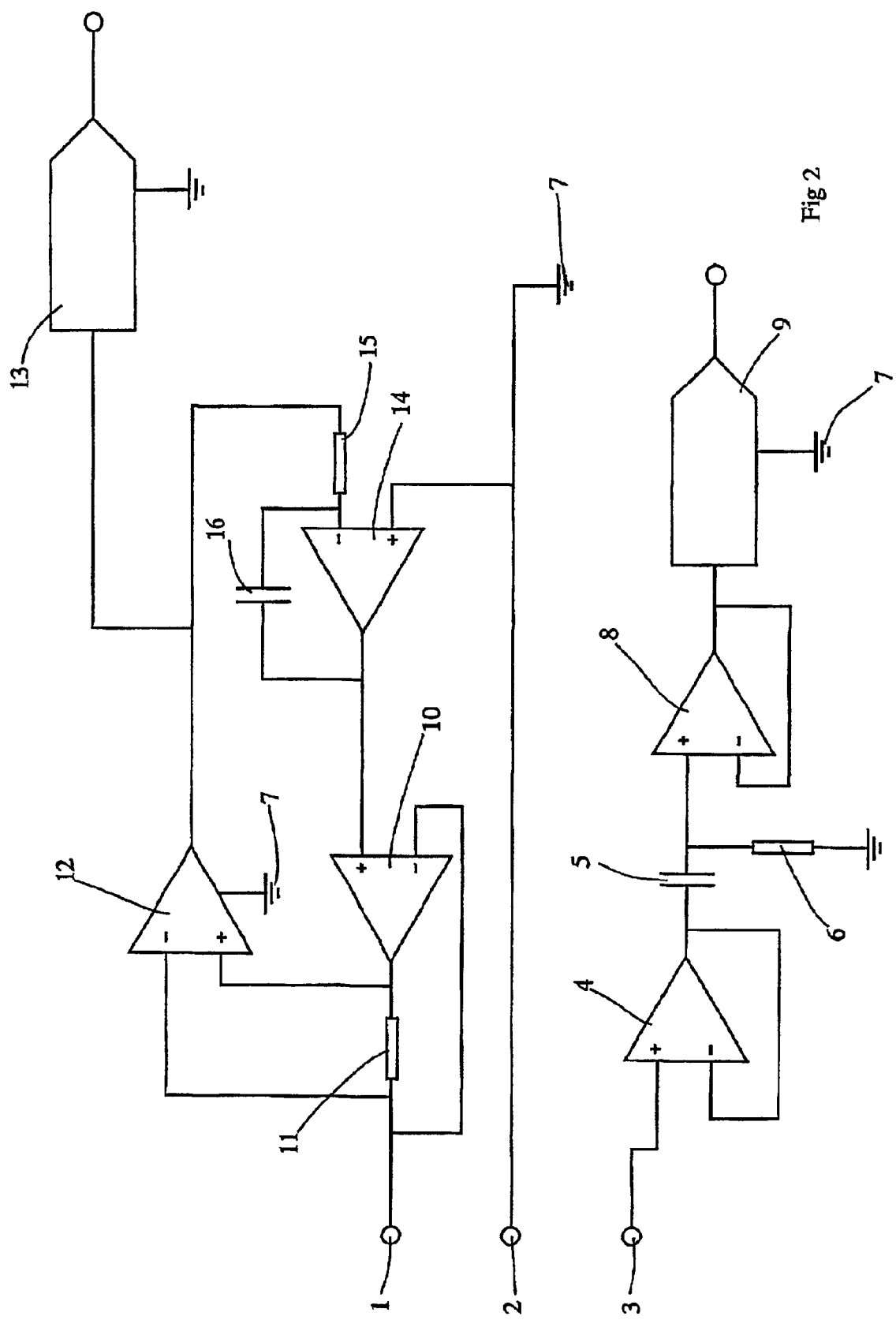
FIG. 2 is an electronic circuit embodying the monitor of FIG. 1.

FIG. 2 shows a specific circuit to implement the arrangement of FIG. 1. Operational amplifier (op-amp) 10, acts to maintain the potential of electrode, 1, at the same potential as it's +ve input. Op-amp 10 will supply whatever positive or negative current is necessary to maintain electrode 1 at this potential. This current passes through resistor 11, and the voltage so developed appears at the differential input terminals of instrumentation amplifier 12. This device takes the differential voltage at its terminals, and refers this voltage to the system ground, 7. This voltage represents the current flowing to electrode 1 and is integrated by the combination of op-amp 14, resistor 15, and capacitor 16.

The voltage at the output of the op-amp 14 thus represents the inverse of the integration of the current flowing to electrode 1, over time. This voltage is connected to the positive input of op-amp 10, to complete the feedback loop.

It can be seen that the feedback loop consisting of op-amps 10 and 14 and instrumentation amplifier 12 act so as to reduce the average current flowing to electrode 1 to zero, as mentioned above. If electrode 1, and electrode, 2, have differing galvanic potentials, this will initially cause relatively high currents to flow. However, the feedback loop will act to change the voltage stored on capacitor, 16, in such a way that the effect of the galvanic potential is removed, and the average current is reduced to zero.

The actual current flowing to electrode 1 is measured using the ADC 13. This converter measures the output of instrumentation amplifier 12 with respect to ground 7.

The current flowing at working electrode 1 returns to the system at the current reference electrode 2. This electrode is connected to ground 7.

The voltage reference electrode 3 is connected to high impedance op-amp 4 that buffers the voltage, prior to being fed to the DC blocking capacitor 5. The voltage on the other side of blocking capacitor 5 is gradually taken to ground 7 via high value resistance 6. The voltage is buffered again in op-amp 8 before being digitised by ADC 9 that measures voltage with respect to ground 7 which in turn is the same potential as the current electrode 2. Thus the voltage being measured by ADC 9 is the AC coupled voltage between inert current electrode 2 and inert voltage electrode 3.

The voltage measuring system consisting of op-amps 4 and 8 act as a block to DC voltage, but allows any AC components to pass through. This is exactly analogous to the current noise measuring system which reduces the DC current to zero but allows AC current noise to pass.

The time constant of the voltage measuring system is determined by the values of resistor 6 and capacitor 5. Typically the time constant is of the order of a minute. Likewise, the time constant of the current measuring system is determined by the values of capacitor 16 and resistor 15. This time constant is of a similar order as the voltage system time constant.

The digitised voltages and currents from ADCs 9 and 13 respectively are fed to a computing device that performs statistical processing to produce corrosion rates using well known methods.

It should be clear that other methods of eliminating the DC element of current flowing to electrode 1 are possible, and within the scope of the current invention. For example, a digital to analogue converter may be used to set the voltage at the +ve input to op-amp 10. In this case, the control loop is completed via the computing device, that may set the DAC in such a way as to reduce the average current flowing to electrode 1 to zero.

It should be further noted that there is no ambiguity about the direction of the current flowing to the electrode, 1, and that this is the only active working electrode. This now enables current and voltage transients to be properly correlated. It has been noted that positive current spikes occur with negative going potential spikes during pitting activity. The computing device may correlate the current and voltage signals in real time, to produce an on-line pitting activity indication, as well as an on-line general corrosion indication.

What is claimed is:

1. A corrosion monitor, comprising a substantially inert reference electrode, a working electrode composed of a material to be monitored, a voltage follower adapted to apply a voltage between the electrodes, wherein the voltage reflects previous values of a current flowing between electrodes, and an integrating circuit for integrating the current, wherein the output of the integrating circuit is introduced to the voltage follower and applied to the working electrode.

2. A corrosion monitor according to claim 1 in which the voltage follower applies a voltage between the electrodes that is proportional to an integration of the current.

3. A corrosion monitor according to claim 1 in which a voltage potential is monitored between the inert reference electrode and a third electrode composed of a substantially insert material.

4. A corrosion monitor according to claim 1, further comprising an ammeter for measuring the current.

5. A corrosion monitor, comprising a substantially inert reference electrode, a working electrode composed of a material to be monitored, a voltage follower adapted to apply a voltage between the electrodes, wherein the voltage reflects previous values of a current flowing between electrodes and an integrating circuit for integrating a current flowing between the inert reference electrode and the working electrode to produce an integrator output, wherein the integrator output is connected to an input of the voltage follower.

6. The corrosion monitor of claim 5, which the voltage applied by the voltage follower is proportional to the integrator output and an output of the voltage follower is introduced to the integrating circuit to produce the integrator output.

* * * * *